US011188620B1

(12) United States Patent
Cai et al.

(10) Patent No.: US 11,188,620 B1
(45) Date of Patent: Nov. 30, 2021

(54) SYSTEM AND METHOD TO IMPROVE DYNAMIC MULTI-CHANNEL INFORMATION SYNTHESIS

(71) Applicant: Quintiles IMS Incorporated, Danbury, CT (US)

(72) Inventors: Yong Cai, Bala Gynwyd, PA (US); Dong Dai, Dresher, PA (US); Yilian Yuan, North Wales, PA (US); Olivier Bouchard, La Défense (FR)

(73) Assignee: IQVIA Inc., Parsippany, NJ (US)

( * ) Notice: Subject to any disclaimer, the term of this patent is extended or adjusted under 35 U.S.C. 154(b) by 679 days.

(21) Appl. No.: 15/381,818

(22) Filed: Dec. 16, 2016

(51) Int. Cl.
*G06F 19/00* (2018.01)
*G06Q 30/00* (2012.01)

(52) U.S. Cl.
CPC ......... *G06F 19/326* (2013.01); *G06Q 30/016* (2013.01)

(58) Field of Classification Search
None
See application file for complete search history.

(56) References Cited

U.S. PATENT DOCUMENTS

| | | | |
|---|---|---|---|
| 8,275,850 B2 | 9/2012 | Kohan et al. | |
| 8,311,863 B1* | 11/2012 | Kemp | G06Q 10/0639 705/7.11 |
| 8,935,753 B1* | 1/2015 | Cha | G16H 40/20 726/4 |
| 2002/0042738 A1* | 4/2002 | Srinivasan | G06Q 30/0255 705/14.43 |
| 2007/0067004 A1* | 3/2007 | Boveja | A61N 1/36017 607/45 |
| 2007/0143186 A1* | 6/2007 | Apple | G06Q 30/02 705/14.48 |
| 2009/0012847 A1* | 1/2009 | Brooks | G06Q 30/0201 705/14.41 |
| 2009/0070129 A1* | 3/2009 | Inbar | G06Q 30/018 705/317 |
| 2009/0177540 A1* | 7/2009 | Quatse | G06Q 30/02 705/14.26 |
| 2009/0254392 A1* | 10/2009 | Zander | G06F 21/6218 705/50 |

(Continued)

*Primary Examiner* — Michael Tomaszewski
*Assistant Examiner* — Jay M. Patel
(74) *Attorney, Agent, or Firm* — Fish & Richardson P.C.

(57) ABSTRACT

Some implementations provide a computer-implemented method that includes retrieving, from a customer relationship (CRM) database, data documenting exposures of healthcare professionals to information of healthcare products from more than one channels and at various time points; processing the retrieved data to model the exposure of each healthcare professional such that an effectiveness of each of the more than one channels for the particular healthcare professional is determined; retrieving, from a prescription database, data recording each healthcare professional prescribing healthcare products at various time points; longitudinally associating the processed data from the customer relationship database and the retrieved data from the prescription database such that a multi-channel CRM and prescription database is generated; and, determining a next healthcare professional to whom information of a particular healthcare product should be directed as well as a channel for the next healthcare professional to receive the information of the particular healthcare product.

21 Claims, 12 Drawing Sheets

(56) References Cited

U.S. PATENT DOCUMENTS

| | | | |
|---|---|---|---|
| 2009/0287837 A1* | 11/2009 | Felsher | G06F 19/328 709/229 |
| 2009/0323918 A1* | 12/2009 | Opaluch | H04M 3/02 379/207.16 |
| 2010/0145792 A1* | 6/2010 | Worthen | G06Q 30/0269 705/14.42 |
| 2012/0069131 A1* | 3/2012 | Abelow | G06Q 10/067 348/14.01 |
| 2012/0072583 A1* | 3/2012 | Kupferman | G06F 11/3495 709/224 |
| 2012/0109689 A1* | 5/2012 | Lee | G06Q 10/06 705/3 |
| 2012/0185264 A1* | 7/2012 | Demogenes | G06Q 50/22 705/2 |
| 2012/0310661 A1* | 12/2012 | Greene | G06Q 10/087 705/2 |
| 2013/0103413 A1* | 4/2013 | Meralli | G06Q 50/22 705/2 |
| 2013/0103465 A1* | 4/2013 | Meralli | G06Q 30/02 705/14.4 |
| 2013/0159021 A1* | 6/2013 | Felsher | G06F 19/328 705/3 |
| 2013/0204700 A1* | 8/2013 | Synett | G06N 5/02 705/14.53 |
| 2013/0218589 A1* | 8/2013 | Lerner | G16H 10/60 705/2 |
| 2014/0031089 A1* | 1/2014 | Opaluch | H04M 3/42051 455/567 |
| 2014/0052475 A1* | 2/2014 | Madan | G06F 19/3418 705/3 |
| 2014/0081669 A1* | 3/2014 | Raduchel | G06Q 50/24 705/3 |
| 2014/0188497 A1* | 7/2014 | Roscoe | G16H 50/30 705/2 |
| 2014/0278507 A1* | 9/2014 | Potter | G06Q 30/0201 705/2 |
| 2014/0280309 A1* | 9/2014 | Anderson | G06F 40/177 707/769 |
| 2014/0327544 A1* | 11/2014 | Ramsdell | G08B 21/24 340/573.1 |
| 2014/0344258 A1* | 11/2014 | Khandelwal | G06F 16/248 707/723 |
| 2014/0357961 A1* | 12/2014 | Meltzer | A61B 5/0002 600/301 |
| 2014/0358576 A1* | 12/2014 | Hoffman | G16H 50/30 705/2 |
| 2015/0046192 A1* | 2/2015 | Raduchel | H04W 8/18 705/3 |
| 2015/0058028 A1* | 2/2015 | Su | G16H 20/10 705/2 |
| 2015/0088540 A1* | 3/2015 | Lo | G06Q 10/10 705/2 |
| 2015/0134346 A1* | 5/2015 | Hyde | G06Q 50/22 705/2 |
| 2015/0244687 A1* | 8/2015 | Perez | G16H 10/60 726/4 |
| 2015/0269355 A1* | 9/2015 | Tidor | G16H 10/20 705/3 |
| 2015/0348591 A1* | 12/2015 | Kaps | G11B 27/17 386/201 |
| 2016/0267224 A1* | 9/2016 | Natarajan | G06N 7/005 |
| 2017/0046736 A1* | 2/2017 | Elmachtoub | G06Q 30/0255 |
| 2017/0161439 A1* | 6/2017 | Raduchel | G06Q 10/063 |

* cited by examiner

302

| Number of products mentioned in one detailing | Percent |
|---|---|
| 1 | 25.14% |
| 2 | 24.73% |
| 3 | 23.60% |
| 4 | 16.57% |
| 5 | 3.40% |
| 6 | 2.13% |
| 7 | 1.63% |
| 8 | 0.97% |
| 9 | 0.63% |
| 10 | 0.43% |
| 11 | 0.30% |
| 12 | 0.45% |
| 15 | 0.03% |

FIG. 3A

| Type of visit | Type of contacts | Percent |
|---|---|---|
| (1) With product presentation | (1) Postal | 46.06% |
| (1) With product presentation | (2) E-Mailin | 37.38% |
| (2) Institutional (No product) | (0) NR | 0.00% |
| (2) Institutional (No product) | (1) Postal | 1.48% |
| (2) Institutional (No product) | (2) E-Mailin | 1.73 |
| (3) Samples | (0) NR | 3.95 |
| (4) Newsletter | (1) Postal | 4.44 |
| (4) Newsletter | (2) E-Mailin | 4.95 |

| Meeting Type | Meeting Type Description | Percent |
|---|---|---|
| 1 | Meeting / debate without meal | 7.74% |
| 2 | National Congress | 6.16% |
| 3 | Conference / symposium | 9.90% |
| 6 | Continuing Medical Education (C.M.E.) | 3.87% |
| 7 | Meal without debate | 2.07% |
| 9 | Seminar | 0.04% |
| 15 | Visit of laboratory production | 0.00% |
| 16 | Leisure / Culture | 0.00% |
| 19 | Meeting / debate with meal | 42.32% |
| 22 | Workshop practice | 0.04% |
| 23 | Hospital visit | 0.00% |
| 25 | Leisure week end | 0.00% |
| 26 | Teaching | 0.00% |
| 34 | Video conference / Video presentation | 0.00% |
| 38 | Satellite Symposium | 0.00% |
| 39 | Meeting by phone | 0.40% |
| 98 | Overseas congress | 6.78% |
| 99 | Other | 1.01% |
| 101 | In hospital product briefing | 18.08% |
| 104 | Internet: automated or pre-recorded broadcast event | 1.10% |
| 105 | Internet: live broadcast event open to multiple attendees | 0.48% |

| HCP Last Name | NBC Dynamic Score At week 54 |
|---|---|
| PATEL | 0.202 |
| KUSHNER | 0.145 |
| RIZZO | 0.124 |
| IVINS | 0.084 |
| GUNASEKARAN | 0.069 |
| BILSKI | 0.068 |
| MOONDRA | 0.060 |
| NAMEY | 0.060 |
| GOODMAN | 0.056 |
| BROWN | 0.051 |
| TUCKER | 0.045 |
| SCHROYER | 0.031 |
| GALLAGHER | 0.028 |
| WALSH | 0.019 |

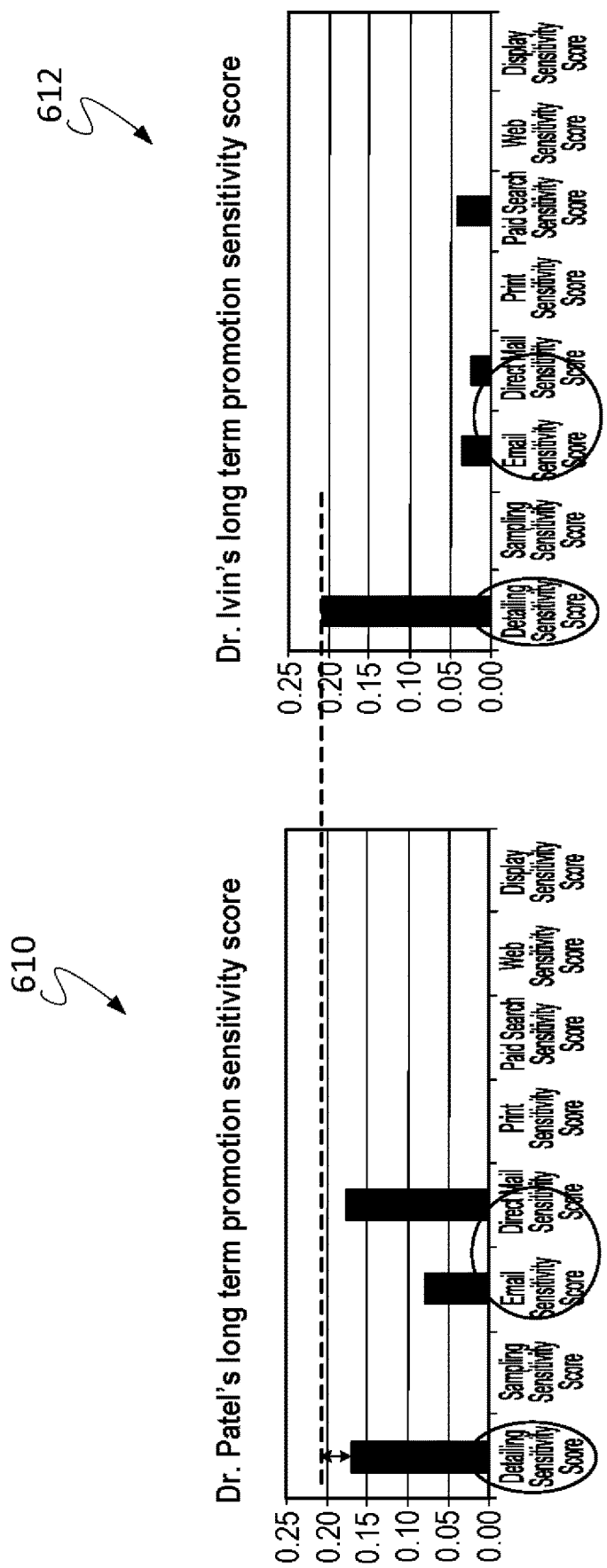

SYSTEM AND METHOD TO IMPROVE DYNAMIC MULTI-CHANNEL INFORMATION SYNTHESIS

BACKGROUND

There is a vast amount of data describing healthcare professionals being exposed to stimulus events. Some tools may display the deluge of historical data in raw format or lightly processed format, without disclosing insights based on intelligent synthesis of information.

SUMMARY

In one aspect, some implementations provide a computer-implemented method that includes: retrieving, from a customer relationship (CRM) database, data documenting exposures of healthcare professionals to information of healthcare products from more than one channels and at various time points; processing the retrieved data to model the exposure of each healthcare professional such that an effectiveness of each of the more than one channels for the particular healthcare professional is determined; retrieving, from a prescription database, data recording each healthcare professional prescribing healthcare products at various time points; longitudinally associating, for each healthcare professional, the processed data from the customer relationship database and the retrieved data from the prescription database such that a multi-channel CRM and prescription database is generated; and based on the multi-channel CRM and prescription database, determining a next healthcare professional to whom information of a particular healthcare product should be directed as well as a channel for the next healthcare professional to receive the information of the particular healthcare product.

Implementations may include one or more of the following features.

Processing the retrieved data to model the exposure of each healthcare professional may include determining the effectiveness of each of the more than one channels in a channel-specific manner. Processing the retrieved data to model the exposure of each healthcare professional may include determining the effectiveness of each of the more than one channels as a decay based on a lapse from a particular time point of the exposure. Processing the retrieved data to model the exposure of each healthcare professional may include consolidating the effectiveness of the more than one channels to generate a combined effectiveness of the more than one channels for each healthcare professional. Processing the retrieved data to model the exposure of each healthcare professional may include correlating exposure of a particular healthcare professional to information of a particular healthcare product at the various time points with the prescription records of the particular healthcare product by the particular healthcare professional at various time points such that prescription records of the particular healthcare professional are consolidated and redundant prescription records are combined.

Determining the next healthcare professional may include: based on the multi-channel CRM and prescription database, generating, for each healthcare professional, a current score for directing information of the healthcare product to the respective healthcare professional; ranking the healthcare professionals according to the current scores for directing information of the healthcare product; and selecting the healthcare professional lodging the highest current score such that information of the particular healthcare product is directed thereto.

The method may include: displaying locations of the ranked healthcare professional on a map. The method may include based on the multi-channel CRM and prescription database and at a subsequent time point, generating, for each healthcare professional, an updated score for directing information of the healthcare product to the respective healthcare professional; ranking the healthcare professionals according to the updated scores for directing information of the healthcare product; and selecting the healthcare professional lodging the highest updated score such that information of the particular healthcare product is directed thereto.

Determining the channel for the next healthcare professional to receive information of the particular healthcare product may include: quantifying, for each channel, a current score for directing information of the healthcare product to the healthcare professional; and selecting the channel with the highest current score for the next healthcare professional to receive information of the particular healthcare product. The method may include: subsequently quantifying, for each channel, an updated score for directing information of the healthcare product to the next healthcare professional; and selecting the channel with the highest updated score for the next healthcare professional to receive information of the particular healthcare product.

In another aspect, some implementations provide computer system in communication with database systems, the computer system comprising at least one processor, wherein the at least one processor is configured to perform the operations of: retrieving, from a customer relationship (CRM) database, data documenting exposures of healthcare professionals to information of healthcare products from more than one channels and at various time points; processing the retrieved data to model the exposure of each healthcare professional such that an effectiveness of each of the more than one channels for the particular healthcare professional is determined; retrieving, from a prescription database, data recording each healthcare professional prescribing healthcare products at various time points; longitudinally associating, for each healthcare professional, the processed data from the customer relationship database and the retrieved data from the prescription database such that a multi-channel CRM and prescription database is generated; and based on the multi-channel CRM and prescription database, determining a next healthcare professional to whom information of a particular healthcare product should be directed as well as a channel for the next healthcare professional to receive the information of the particular healthcare product.

Implementations may include one or more of the following features.

Processing the retrieved data to model the exposure of each healthcare professional may include determining the effectiveness of each of the more than one channels in a channel-specific manner. Processing the retrieved data to model the exposure of each healthcare professional may include determining the effectiveness of each of the more than one channels as a decay based on a lapse from a particular time point of the exposure. Processing the retrieved data to model the exposure of each healthcare professional may include consolidating the effectiveness of the more than one channels to generate a combined effectiveness of the more than one channels for each healthcare professional. Processing the retrieved data to model the exposure of each healthcare professional may include correlating exposure of a particular healthcare professional to information of a particular healthcare product at the various time points with the prescription of the particular healthcare product by the particular healthcare professional at various time points.

Determining the next healthcare professional may include based on the multi-channel CRM and prescription database, generating, for each healthcare professional, a current score for directing information of the healthcare product to the respective healthcare professional; ranking the healthcare professionals according to the current scores for directing information the healthcare product; and selecting the healthcare professional lodging the highest current score such that information of the particular healthcare product is directed thereto. The operations may further include: displaying locations of the ranked healthcare professional on a map. The operations may further include: based on the multi-channel CRM and prescription database and at a subsequent time point, generating, for each healthcare professional, an updated score for directing information of the healthcare product to the respective healthcare professional; ranking the healthcare professionals according to the updated scores for directing information of the healthcare product; and selecting the healthcare professional lodging the highest updated score such that information of the particular healthcare product is directed thereto.

Determining the channel for the next healthcare professional to receive information of the particular healthcare product may include: quantifying, for each channel, a current score for directing information of the healthcare product to the healthcare professional; and selecting the channel with the highest current score for the next healthcare professional to receive information of the particular healthcare product.

The operations may further include: subsequently quantifying, for each channel, an updated score for directing information of the healthcare product to the next healthcare professional; and selecting the channel with the highest updated score for the next healthcare professional to receive information of the particular healthcare product.

In yet another aspect, some implementations provide A computer-readable medium comprising software instructions that, when executed by a computer, causes the computer to perform the operations of: retrieving, from a customer relationship (CRM) database, data documenting exposures of healthcare professionals to information of healthcare products from more than one channels and at various time points; processing the retrieved data to model the exposure of each healthcare professional such that an effectiveness of each of the more than one channels for the particular healthcare professional is determined; retrieving, from a prescription database, data recording each healthcare professional prescribing healthcare products at various time points; longitudinally associating, for each healthcare professional, the processed data from the customer relationship database and the retrieved data from the prescription database such that a multi-channel CRM and prescription database is generated; and based on the multi-channel CRM and prescription database, determining a next healthcare professional to whom information of a particular healthcare product should be directed as well as a channel for the next healthcare professional to receive the information of the particular healthcare product.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIGS. 3A to 3C show examples of data from different channels in the example illustrated in FIG. 2.

FIGS. 6A to 6F show examples of dynamic scores for determining the next best customer (NBC) at week 54.

Like reference symbols in the various drawings indicate like elements.

DETAILED DESCRIPTION

Figure 1:
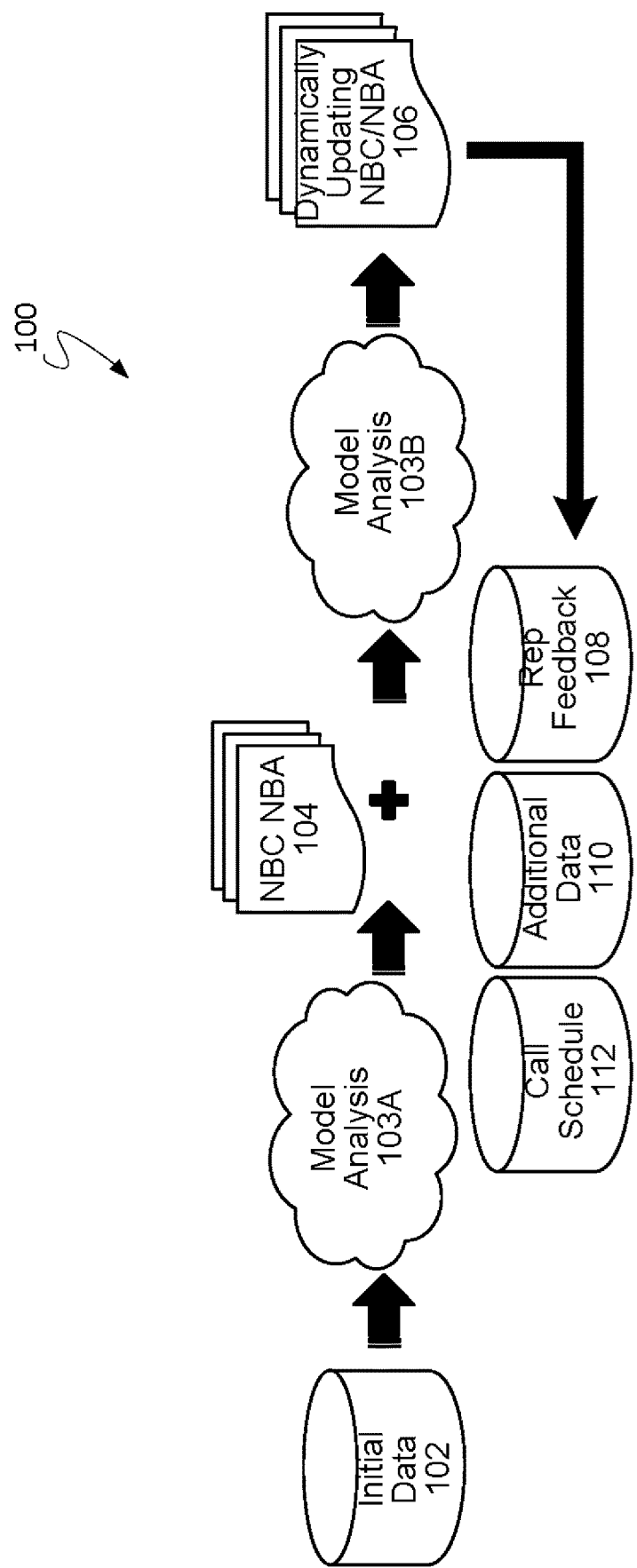
FIG. 1 illustrates an example of continuously processing input data and iteratively improving prediction of next best customer (NBC) and next best action (NBA).

This disclosure generally describes a system and method to improve dynamic multi-channel information synthesis. In some implementations, incoming information are grouped into various channels for a particular customer, such as a healthcare professional including a physician, a dentist, a specialist, a registered nurse, or a licensed professional authorized to prescribe a medicine. Incoming information at each channel may operate to impact recipient with different dynamics, each having characteristic and distinctive responses to stimuli events at the respective channel. In some examples, incoming information may be derived from one or more customer relationship management (CRM) databases. The incoming information may include, for example, healthcare professional receiving a stimulus during an event, such as detailing, mailing, and meeting. The event may have transpired at a particular time to expose the healthcare professional to information of healthcare products, such as benefits or adverse effects of healthcare products. As the incoming information is being dissected, data from a prescription database may be consolidated with the incoming information to correlate exposure of a particular healthcare professional to information of the particular healthcare product with the prescription record of the particular healthcare product by the particular healthcare professional. The correlation may generate a longitudinally associated multi-channel CRM and prescription data records. In some instances, the prescription data records may include prescription and claims record as filed by pharmacies. The correlation may operate based on the same healthcare professional. The consolidation may combine redundant prescription records that would otherwise be attributed to different healthcare professionals simply because the prescriptions were submitted at different specialties or facilities, even when by the same healthcare professional.

As discussed, the consolidation generates longitudinally combined data for each healthcare professional his/her exposure to healthcare product information and actual prescription record. The longitudinally assembled data from various healthcare professionals may be analyzed at a given time to determine who would be the next best customer and what would be the next best action to take to expose the healthcare professional to information of a particular healthcare product. The calculus may quantitatively generate a score for each healthcare professional with regard to the particular healthcare product. The dynamic scores from various healthcare professionals may be ranked and the healthcare professional with the highest score may be chosen as the next best customer. The calculus may then determine the next best action for this particular next best customer. This next best action for the particular best customer may be determined by quantifying a score for the impact of each channel on this particular healthcare professional. The quantification may factor in earlier stimulus events in view of the corresponding dynamics describing the stimulus impact. The dynamic score for each channel may be compared and the next best action may be picked from the channel with the highest dynamic score for impact.

FIG. 1 illustrates an example 100 of continuously processing input data and iteratively improving prediction of next best customer (NBC) and next best action (NBA). In this example, input data 102 may be synthesized from historical data recording exposure of healthcare professionals to stimuli events as well as prescription data showing the actual prescription record for a given healthcare professional.

Figure 2:
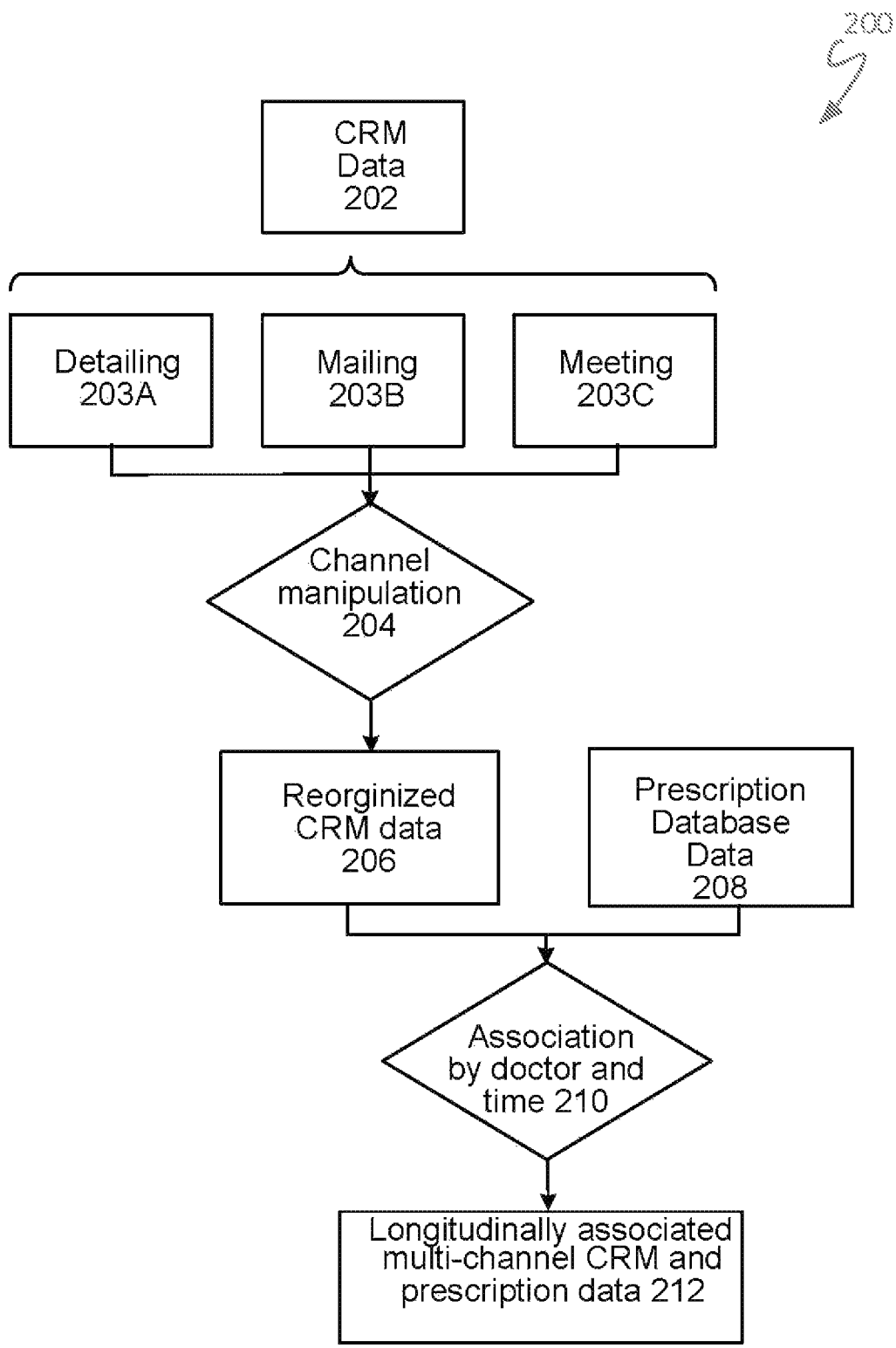
FIG. 2 is a diagram illustrating an example of consolidating customer relationship management (CRM) data and prescription record data to model input data at various input channels.

Referring to FIG. 2, diagram 200 illustrates an example of consolidating customer relationship management (CRM) database data 202 and prescription record data 208 to model input data at various input channels. In this diagram, CRM database data 202 includes detailing data 203A, mailing data 203B, and meeting data 203C. Detailing refers to the activity of pharmaceutical sales representatives (reps) when they make calls or office visits to healthcare professional and provide them with "details"—approved scientific information, benefits, side effects, or adverse events—related to a healthcare product, for example, a prescription drug. Detailing data 203A records the time, sales person, healthcare professional, and target healthcare product being discussed. An example composition of detailing data 203A is shown in FIG. 3A. Here, the break-down percentages for various healthcare products discussed at the detailing events are tabulated in table 302. The detailing event is one form of stimuli in which a sales person can visit a healthcare professional's office to particularly discuss the target healthcare product. The detailing event has its own characteristic dynamic model describing a temporal effect.

The mailing data 203B records the time and all contextual information for mailing product information for a target healthcare product to a target healthcare information. The mailing event is another form of stimuli that is modelled by its own characteristic dynamics. An example showing the percentage for each types of mainlining events is shown in FIG. 3B. Here, the mailing events tabulated in table 304 generally cover events when printed material reaches a target healthcare professional to present information of a particular healthcare product. The events include mail events (such as postal events) and email events (as a form of electronic transmission). The email events may refer to email that include links to or contents of a healthcare product. The break-down of these mailing events generally demonstrate the composition and percentage quantity of various mailing events.

The meeting data 203C records the time and all contextual information for a professional meeting during which one or more target healthcare professionals receives information regarding a particular healthcare product. The meeting is yet another form of stimuli, each of which can be modelled by its own characteristic dynamics. An example showing the percentage make-up for each meeting type is demonstrated in table 306 of FIG. 3C. The specific meeting types cover meeting/debate with meal, meeting/debate without meal, in hospital product briefing, national congress, conference symposium, continuing medical education, seminar, telephonic conference/meeting, etc. Each type can have its own characteristic dynamic models.

In diagram 200, CRM database data 202 is analyzed by a channel manipulation process 204 to produce reorganized CRM data 206. CRM data 206 enumerates, for each healthcare provider, the time, the channel, and the effective number of visits for exposing the healthcare provider to information of a particular healthcare product.

This reorganized CRM data 206 and the prescription database data 208 may then be compared. The prescription database data 208 may generally include documented prescription record and claims data for a particular healthcare product. The prescriptions may be initiated by a specific healthcare professional at various times. The prescription database may include a database of records of prescription fulfillment at pharmacy stores. The records are generally accumulated as patients work with their pharmacists to fill prescription scripts for healthcare products, such as prescription drugs. The prescription scripts may be written by patients' healthcare providers. The prescription database may include records showing the specific healthcare professional practicing at various locations or specialties. The prescription database may have each healthcare professional as anonymous or de-identified entities to preserve privacy for the healthcare professionals. As to each recipient patient, the prescription database does not reveal the identity of the patients. In other words, the prescription database is devoid of identity information that can be used to reveal patient's true and actual identity. In some instances, the comparison of reorganized CRM data 206 and prescription database data 208 may be based on the particular healthcare provider as well as the time points for various stimuli events (i.e., exposing times) and the various prescription time points. In other words, reorganized CRM data 206 and prescription database data 208 can be associated by healthcare professional and the various time instants corresponding to an exposure event or a prescription fulfilment (210) such that a serialized record for each healthcare professional is generated showing the longitudinally associated healthcare professional CRM and prescription data 212. While some healthcare professionals may practice at various institutions and show up as apparently different entities in the CRM database data 202, the longitudinally associated healthcare professional CRM and prescription data 212 may have the records for the same healthcare professional coalesced into one string or records. The coalescing may be based on the encrypted string for each healthcare professional in the prescription database data 208. This encrypted string is expected to be unique for each healthcare professional. By virtue of the encrypted string, the true identity of each healthcare professional may remain concealed in the prescription database data 208. Through a mapping between the encrypted string and the identity information of the healthcare professional, the longitudinally associated healthcare professional CRM and prescription data 212 may be generated. In some implementations, the mapping (or bridging) is updated monthly to reflect changes in the healthcare professional information, such as change of practice status, specialty updates. In other implementations, the update interval may vary.

Returning to FIG. 1, input data 102 may be subject to modelling process 103A. In one example, the modeling process 103A may operate on the longitudinally associated multi-channel CRM and prescription data 212. In this example, the stimuli events for one particular healthcare professional may be grouped into different channels and serialized on a time-basis such that the prescription pattern from the particular healthcare professional is viewed in the context of the stimuli events. Moreover, the prescription pattern for each healthcare product may be fitted against a corresponding dynamic model that characterizes the temporal impact of stimuli events that had transpired before the recorded prescription fulfillment.

Figure 4A:
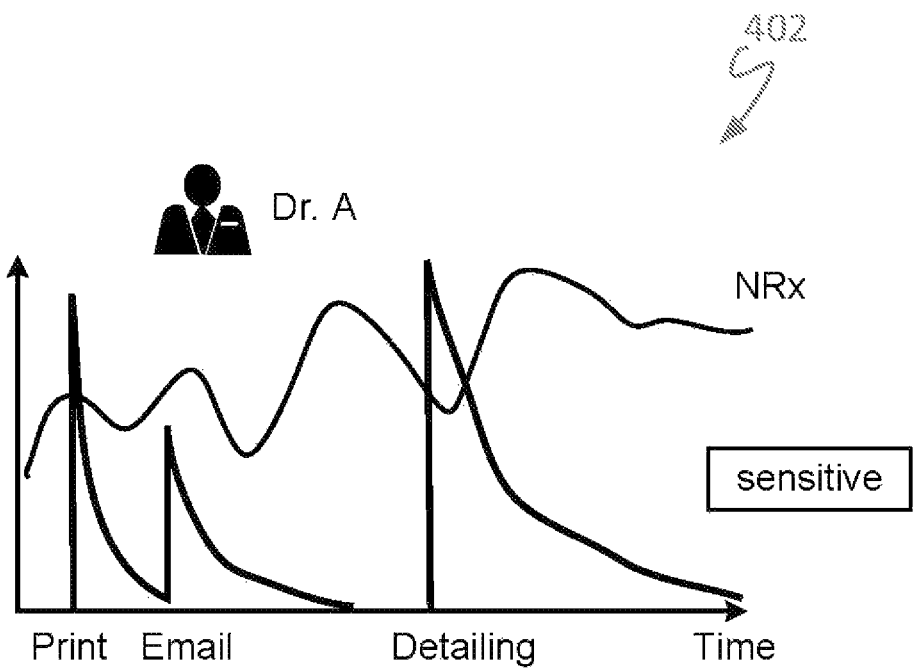
FIGS. 4A and 4B show examples of dynamic analysis as applied to two healthcare professionals in responding to temporal stimulus events.
Figure 4B:
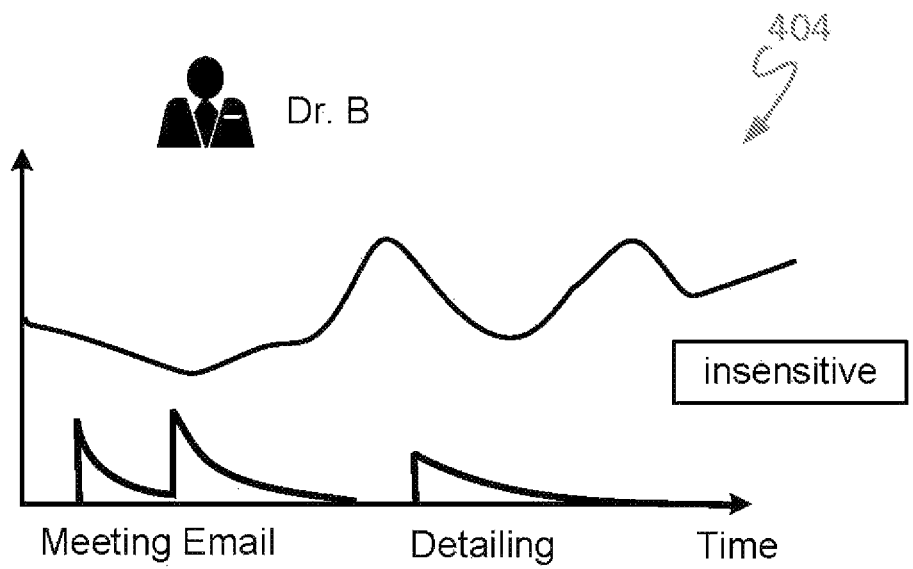
Figure 5A:
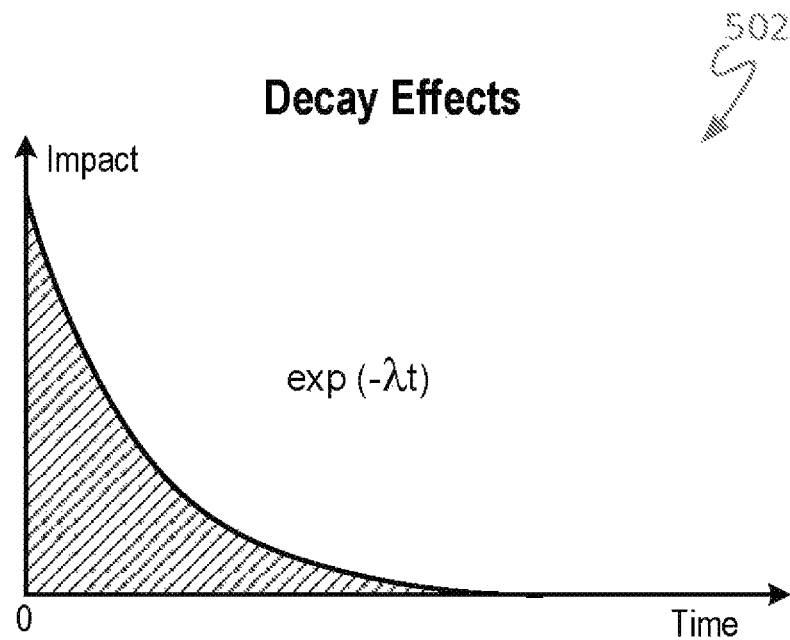
FIGS. 5A to 5E show examples of parameters quantifying the dynamics illustrated by the examples from FIGS. 4A and 4B.
Figure 5B:
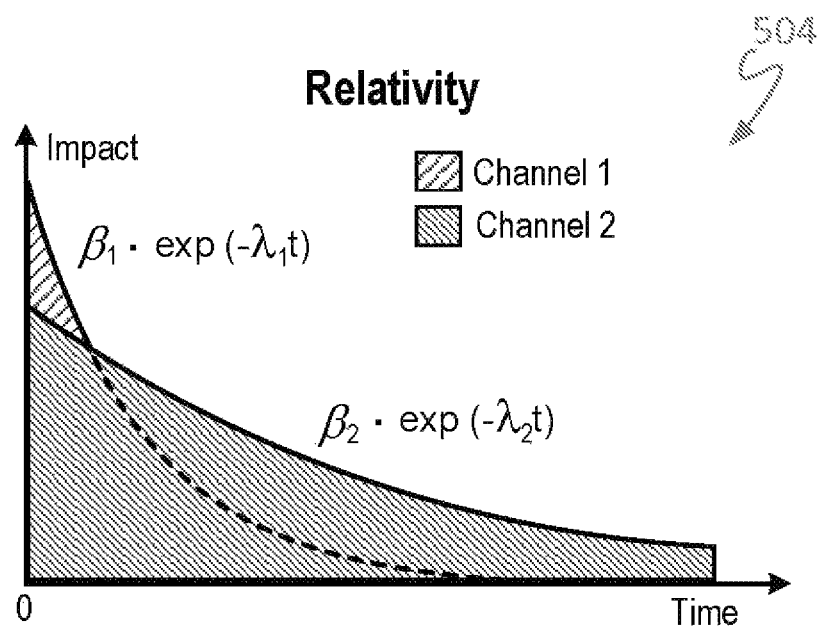
Figure 5C:
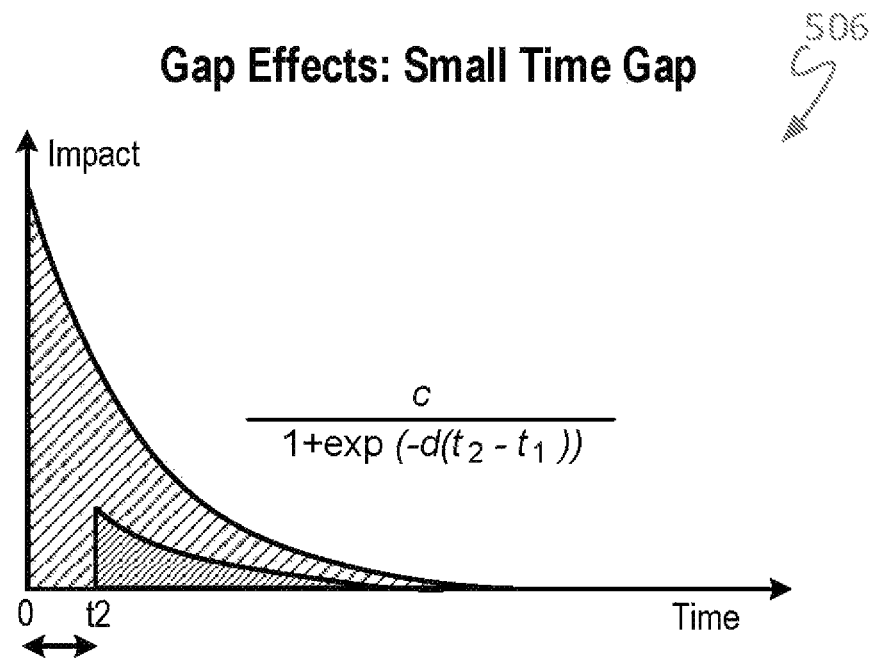
Figure 5D:
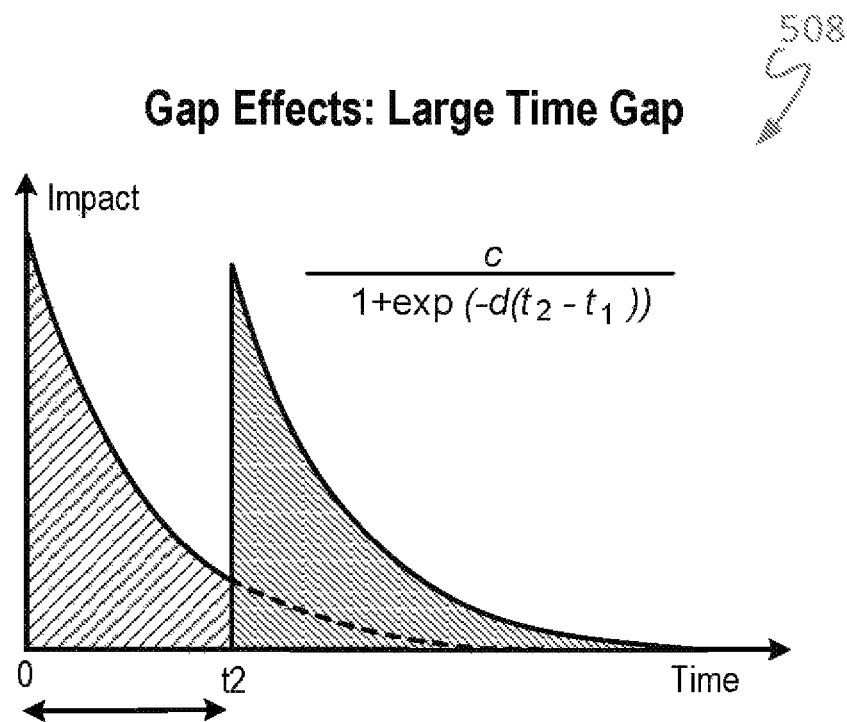

Referring to FIGS. 4A and 4B, examples of dynamic analysis are shown. These examples demonstrate dynamic analysis as applied to two healthcare professionals in responding to temporal stimulus events. For Dr. A, the diagram 402 in FIG. 4A shows a temporal curve of prescription record for a particular healthcare product that Dr. A has prescribed. The response model for printing event, email event, detailing event with regard to Dr. A are displayed in an superimposing manner. Likewise, the diagram 404 in FIG. 4B shows the corresponding temporal curve of prescription record for the particular healthcare product that Dr. B has prescribed as well as the overlapping response models for printing event, email event, and detailing event. As shown, each event follows a decay curve indicating that its impact is relatively most profound immediately following the event. The actual prescription record can be modeled as a result of joint contributions from all the stimuli events. As indicated, Dr. A is classified as being sensitive to the stimuli events by virtue of, for example, a relatively good quality match. The matching quality may be based on characteristics of the fitting process FIGS. 5A to 5E show examples of parameters quantifying the dynamics illustrated by the examples from FIGS. 4A and 4B. The diagram 502 in FIG. 5A demonstrates a monoexponential decay to model the decay effect of a stimulus event. In the diagram 504 of FIG. 5B, two mono-exponential decays with distinct decay constants are compared. One mono-exponential decay has a relatively longer decay constant while the other has a relatively shorter decay constant. FIGS. 5C and 5D show the gap effect when two stimuli events occur in succession. Technically, the phenomenon may be referred to as forgetting effects. In FIG. 5C, the time gap of t2–t1 is small, the effect from first stimuli has not been "forgotten" yet. In this illustration, the impact from second stimuli is overshadowed by the first stimuli. Therefore, its impact is small. In FIG. 5D, however. the time gap of t2–t1 is relatively large. The impact from first stimuli has been 'forgotten' by the time of t2 and therefore more impact is expected from the second stimuli.

Figure 5E:
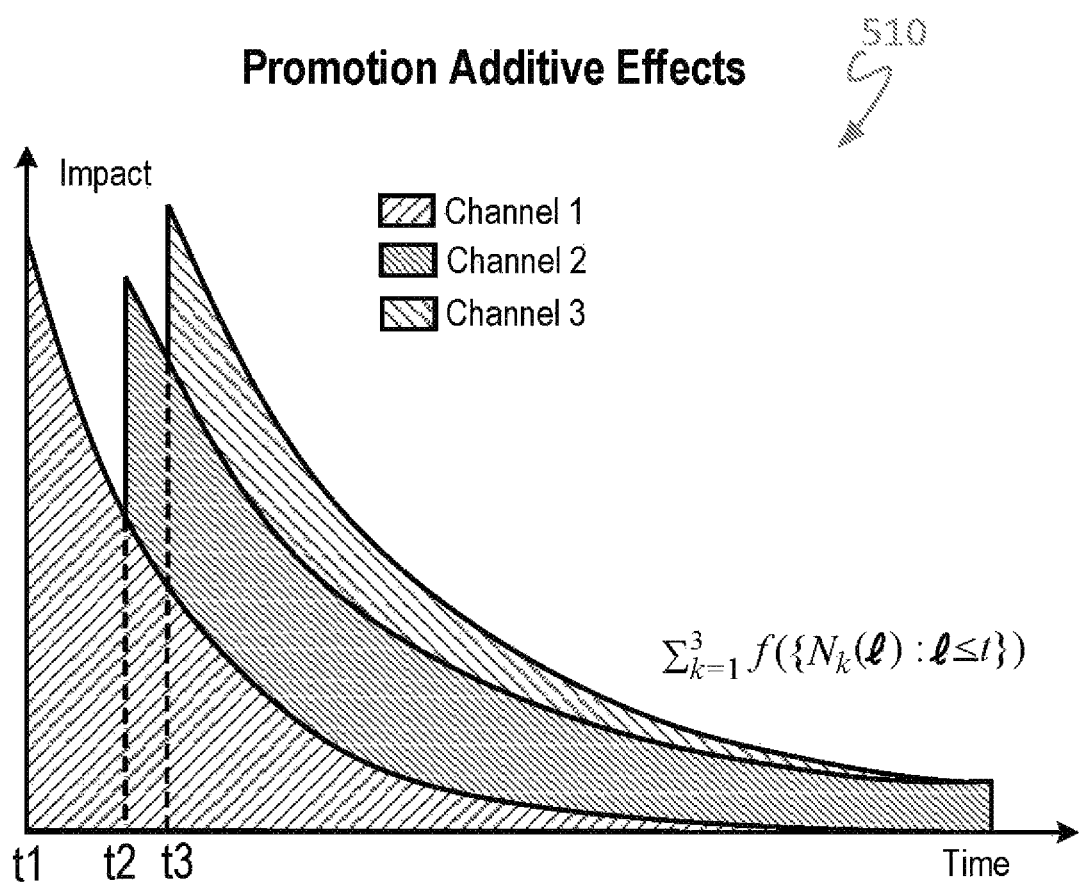

FIG. 5E shows the additive effect of several stimuli events. As discussed above, the actual prescription record may be modeled as resulting from the joint contributions of several stimuli events. The diagram 510 of FIG. 5E demonstrates the summation of three dynamic models.

Returning to FIG. 1, the next-best-customer (NBC) and next-best-action (NBA) 104 may be obtained by applying the modelling process 103A to input data 102. Referring to FIGS. 6A to 6F, dynamic scores may be generated to render such determinations. In the example of FIGS. 6A to 6F, the next best customer (NBC) and next-best-action (NBA) are determined for week 54.

Figures 6A, 6B:
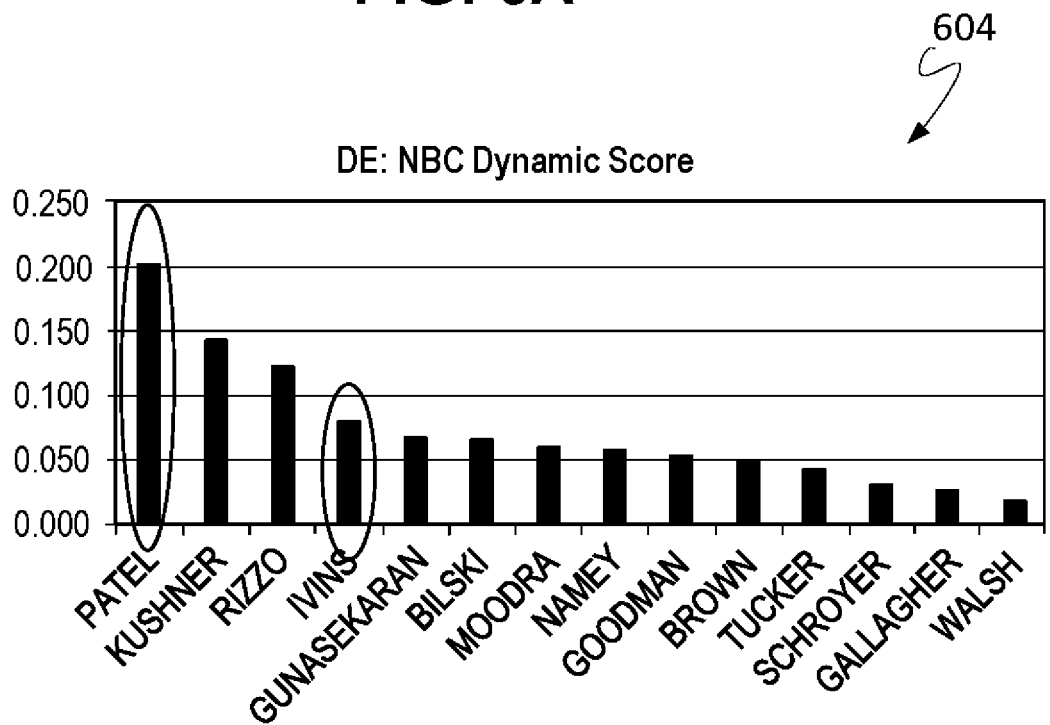

FIGS. 6A to 6B show the generated NBC scores based on, for example, the model process 103A. The generated NBC scores dynamically predict, at the specific instant, the rankings of all healthcare professionals in the database. Specifically, at week 54, Dr. Patel is ranked No. 1 with a score of 0.202 while Dr. Ivins is ranked as the 4$^{th}$ with a score of 0.084, as shown in table 602 and chart 604. In some implementations, the ranked information may be displayed on a map that shows the location of various healthcare professional under consideration for exposure events. The localization of ranking results are advantageous when planning office visits to the various healthcare professionals in the area who are sensitive to the exposure events and are due for some exposure events.

Figure 6C:
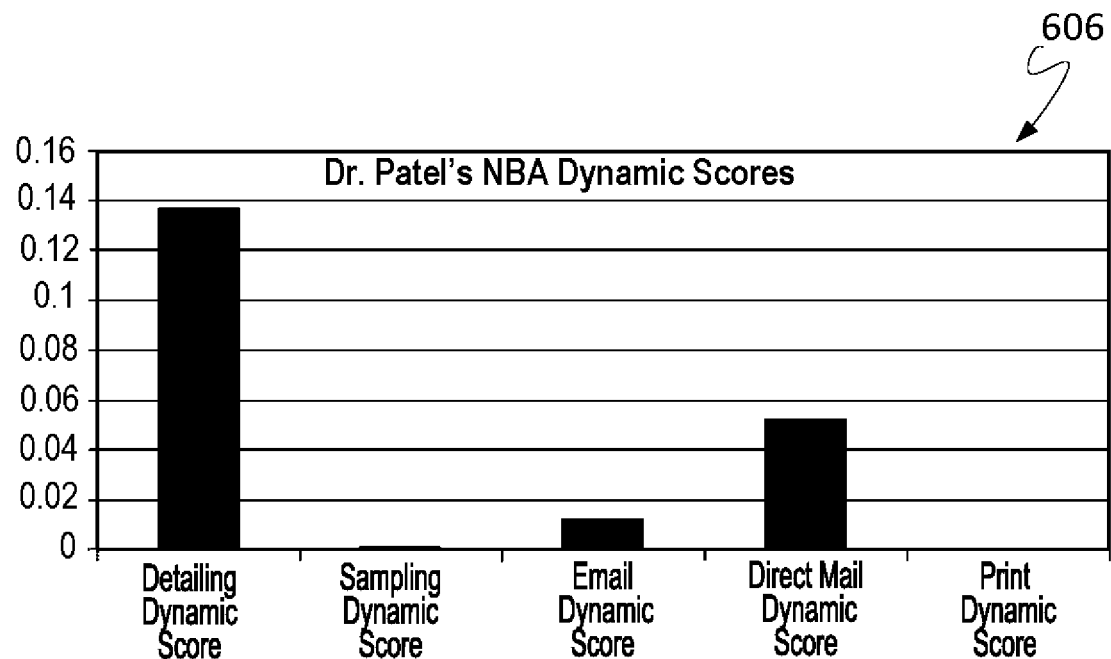
Figure 6D:
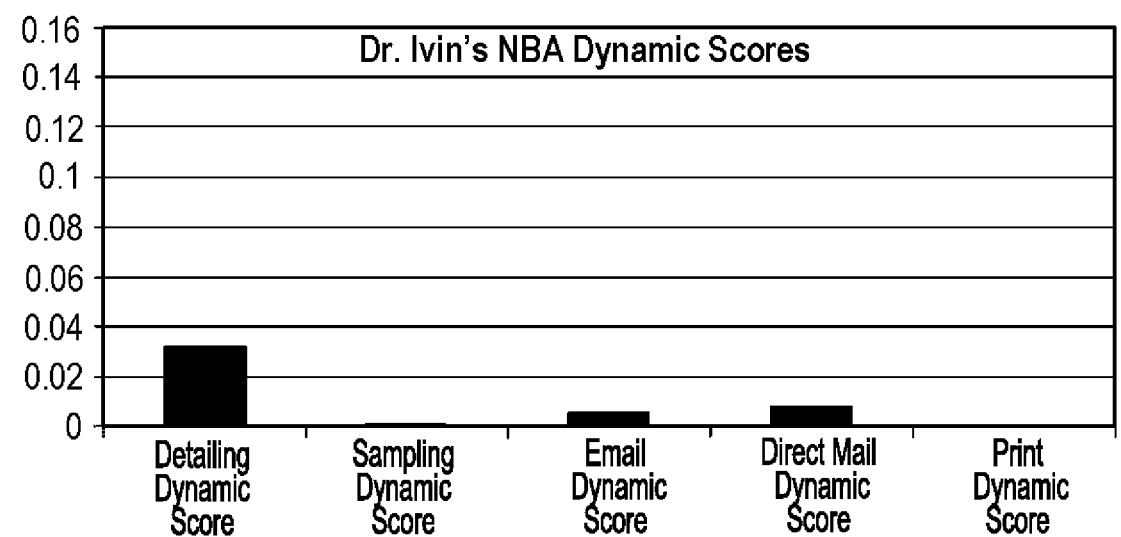

FIGS. 6C to 6D show the generated NBA scores for Drs. Patel and Ivins based on, for example, the model process 103A. The generated NBA scores show, at the specific instant, the ranking of all actions to take to target each healthcare professional. Here, the chart 606 of FIG. 6C shows the dynamic scores for Dr. Patel. As indicated, detailing, emailing and direct mailing represent viable options. The chart 608 of FIG. 6D shows the dynamic scores for Dr. Ivin in which only detailing may represent a viable option.

More interestingly, FIGS. 6E and 6F show the long term sensitivity scores of Dr. Patel and Dr. Ivins, respectively. The chart 610 of FIG. 6E illustrates the long term sensitivity scores of Dr. Patel to each type of stimuli events. The sensitivity scores for detailing, emailing, and direct mailing may be factored into the calculus for selecting a particular exposure event to direct product information. The chart 612 of FIG. 6F illustrates the long term sensitivity scores of Dr. Ivins with regard to the same types of stimuli events. Here, Dr. Ivins exhibits a strong inclination to detailing events. Indeed, the comparison shows Dr. Ivins is more sensitive to detailing events than Dr. Patel. Such doctor-to-doctor variation may be insightful when choosing between two healthcare professionals.

Returning to FIG. 1, the NBC/NBA data 104 may form a recommendation for pharmaceutical representatives to consider. While promotional activities are taken by these representatives, for example, in view of the recommendations, the modeling process 103B may be applied based on the NBC/NBA recommendation 104 and in view of newly available information such as representative feedback 108, additional data 110, and/or call schedule 112. Representative feedback 108 may refer to feedback from detailing events when a particular healthcare professional reveals more insight of his or her prescription preference. Additional data 110 may include customer data that has surfaced after NBC/NBA data 104 becomes available. Examples may include when extra doctors who are newly exposed to stimuli enter into the modeling process, when existing doctors are exposed to more stimuli, or when the match process captures new prescription information of healthcare products. Call schedule data 112 may refer to, for example, calls scheduled but not yet committed, to channel information of a particular healthcare product to healthcare professionals. The NBC/NBA recommendation 104 as well as representative feedback 108, additional data 110, and call schedule 112 may be iteratively analyzed via the modeling process 103B such that updated NBC/NBA recommendations are generated dynamically (106). This process factors in the last recommendations, actions taken, actions scheduled, newly available feedback, and any other additional data. The iterative nature to dynamically generate the next recommendations for NBC/NBA improves the freshness of the next recommendations. The iterative process also factors in the sensitivity of each healthcare professional with respect to the exposures.

Like reference symbols in the various drawings indicate like elements.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method, the method comprising:
　associating, for each of a plurality of healthcare professionals, a plurality of first records and a plurality of second records into a longitudinal record based on anonymized information unique for each healthcare professional,
　　wherein the plurality of first records are from a customer relationship management (CRM) database, and indicate each of the plurality of healthcare professionals receiving information of a healthcare product from a plurality of channels, and
　　wherein the plurality of second records are from a prescription database, and show prescription records of each healthcare professional for the healthcare product;
　determining, for each of the plurality of healthcare professional and based on the longitudinal record, an individual effect when information of the healthcare product is received from a channel, and a combined effect from the plurality of channels,
　　wherein the individual effect has a magnitude decreasing after the information of the healthcare product is received, and
　　wherein the combined effect on the healthcare professional is a summation of individual effects from the pluralities of channels;
　displaying, on a user interface, a dynamic ranking of the healthcare professionals based on the combined effect, wherein a map presented on the user interface graphically displays each of the dynamically ranked healthcare professionals at a location on the map relative to a location of the user;
　in response to a user selecting a healthcare professional from the dynamic ranking, displaying, on the user interface, a lineup of the plurality of channels for the healthcare professional to receive the information of the healthcare product, based on the individual effects through the plurality of channels; and
　scheduling a communication with the healthcare professional through a channel chosen by the user such that the information of the healthcare product is directed thereto.

2. The method of claim 1, wherein determining the combined effect comprises determining the individual effect of each of the plurality of channels in a channel-specific manner as the plurality of first records at the CRM database and the plurality of second records at the prescription database are being updated.

3. The method of claim 1, wherein determining the combined effect comprises determining the individual effect of each of the plurality of channels as exponentially decreasing at a channel specific rate according to an elapsed time since the healthcare professional received information of the healthcare product, which channel-specific rate is determined, at least in part, by the plurality of second records at the prescription database.

4. The method of claim 1, wherein determining the combined effect comprises consolidating the individual effect of each of the plurality of channels to generate the combined effect of the plurality of channels for each healthcare professional.

5. The method of claim 1, wherein determining the combined effect comprises correlating each instance in which the healthcare professional received information of the healthcare product with the prescription records of the healthcare product by the healthcare professional such that prescription records of the healthcare professional are consolidated; and redundant prescription records are combined.

6. The method of claim 1, wherein displaying the dynamic ranking comprises:
based on the combined effect determined from the associated first and second records, generating, for each healthcare professional, a current score for directing information of the healthcare product to the healthcare professional; and
ranking the healthcare professionals according to the current scores for directing information of the healthcare product.

7. The method of claim 6, further comprising:
based on the combined effect determined from the associated first and second records, and at a subsequent time point, generating, for each healthcare professional, an updated combined effect for directing information of the healthcare product to the healthcare professional; and
ranking the healthcare professionals according to the updated combined effect for directing information of the healthcare product to each healthcare professional.

8. The method of claim 1, wherein displaying the lineup of the plurality of channels comprises:
determining, for each channel, a current individual effect for directing information of the healthcare product to the healthcare professional.

9. The method of claim 8, further comprising:
subsequently determining, for each channel, an updated individual effect for directing information of the healthcare product to the healthcare professional.

10. A computer system in communication with database systems, the computer system comprising at least one processor, wherein the at least one processor is configured to perform operations of:
associating, for each of a plurality of healthcare professionals, a plurality of first records and a plurality of second records into a longitudinal record based on anonymized information unique for each healthcare professional,
wherein the plurality of first records are from a customer relationship management (CRM) database, and indicate each of the plurality of healthcare professionals receiving information of a healthcare product from a plurality of channels, and
wherein the plurality of second records are from a prescription database, and show prescription records of each healthcare professional for the healthcare product;
determining, for each of the plurality of healthcare professional and based on the longitudinal record, an individual effect when information of the healthcare product is received from a channel, and a combined effect from the plurality of channels,
wherein the individual effect has a magnitude decreasing after the information of the healthcare product is received, and
wherein the combined effect on the healthcare professional is a summation of individual effects from the pluralities of channels;
displaying, on a user interface, a dynamic ranking of the healthcare professionals based on the combined effect, wherein a map presented on the user interface graphically displays each of the dynamically ranked healthcare professionals at a location on the map relative to a location of the user;
in response to a user selecting a healthcare professional from the dynamic ranking, displaying, on the user interface, a lineup of the plurality of channels for the healthcare professional to receive the information of the healthcare product, based on the individual effects through the plurality of channels; and
scheduling a communication with the healthcare professional through a channel chosen by the user such that the information of the healthcare product is directed thereto.

11. The computer system of claim 10, wherein determining the combined effect comprises determining the individual effect of each of the plurality of channels in a channel-specific manner as the plurality of first records at the CRM database and the plurality of second records at the prescription database are being updated.

12. The computer system of claim 10, wherein determining the combined effect comprises determining the individual effect of each of the plurality of channels as exponentially decreasing at a channel specific rate according to an elapsed time since the healthcare professional received information of the healthcare product, which channel-specific rate is determined, at least in part, by the plurality of second records at the prescription database.

13. The computer system of claim 10, wherein determining the combined effect comprises consolidating the individual effect of each of the plurality of channels to generate the combined effect of the plurality of channels for each healthcare professional.

14. The computer system of claim 10, wherein determining the combined effect comprises correlating each instance in which the healthcare professional received information of the healthcare product with the prescription records of the healthcare product by the healthcare professional such that prescription records of the healthcare professional are consolidated; and redundant prescription records are combined.

15. The computer system of claim 10, wherein displaying the dynamic ranking comprises:
based on the combined effect determined from the associated first and second records, generating, for each healthcare professional, a current score for directing information of the healthcare product to the healthcare professional; and
ranking the healthcare professionals according to the current scores for directing information of the healthcare product.

16. The computer system of claim 15, wherein the operations further comprise:
based on the combined effect determined from the associated first and second records, and at a subsequent time point, generating, for each healthcare professional, an updated combined effect for directing information of the healthcare product to the healthcare professional; and
ranking the healthcare professionals according to the updated combined effect for directing information of the healthcare product to each healthcare professional.

17. The computer system of claim 10, wherein displaying the lineup of the plurality of channels comprises:

determining, for each channel, a current individual effect for directing information of the healthcare product to the healthcare professional.

18. The computer system of claim 17, wherein the operations further comprise:

subsequently determining, for each channel, an updated individual effect for directing information of the healthcare product to the healthcare professional.

19. A computer-readable medium comprising software instructions that, when executed by a computer, causes the computer to perform operations of:

associating, for each of a plurality of healthcare professionals, a plurality of first records and a plurality of second records into a longitudinal record based on anonymized information unique for each healthcare professional, wherein the plurality of first records are from a customer relationship management (CRM) database, and indicate each of the plurality of healthcare professionals receiving information of a healthcare product from a plurality of channels, and wherein the plurality of second records are from a prescription database, and show prescription records of each healthcare professional for the healthcare product;

determining, for each of the plurality of healthcare professional and based on the longitudinal record, an individual effect when information of the healthcare product is received from a channel, and a combined effect from the plurality of channels, wherein the individual effect has a magnitude decreasing after the information of the healthcare product is received, and wherein the combined effect on the healthcare professional is a summation of individual effects from the pluralities of channels;

displaying, on a user interface, a dynamic ranking of the healthcare professionals based on the combined effect, wherein a map presented on the user interface graphically displays each of the dynamically ranked healthcare professionals at a location on the map relative to a location of the user;

in response to a user selecting a healthcare professional from the dynamic ranking, displaying, on the user interface, a lineup of the plurality of channels for the healthcare professional to receive the information of the healthcare product, based on the individual effects through the plurality of channels; and scheduling a communication with the healthcare professional through a channel chosen by the user such that the information of the healthcare product is directed thereto.

20. The computer-implemented method of claim 1, wherein the dynamic ranking rearranges an order of the healthcare professionals such that the healthcare professional with the highest combined effect becomes the highest ranked healthcare professional as the CRM database and the prescription database are being updated.

21. The computer-implemented method of claim 1, further comprising:

in response to the user selecting an additional healthcare professional from the dynamic ranking on the user interface, displaying, on the user interface, a lineup of the plurality of channels for each of the healthcare professional and the additional healthcare professional to receive the information of the healthcare product, the lineup for each of the healthcare professionals showing the individual effects from the plurality of channels.

* * * * *

UNITED STATES PATENT AND TRADEMARK OFFICE
CERTIFICATE OF CORRECTION

| | | |
|---|---|---|
| PATENT NO. | : 11,188,620 B1 | Page 1 of 1 |
| APPLICATION NO. | : 15/381818 | |
| DATED | : November 30, 2021 | |
| INVENTOR(S) | : Cai et al. | |

It is certified that error appears in the above-identified patent and that said Letters Patent is hereby corrected as shown below:

On the Title Page

Item (72) Inventors: Line 1, delete "Bala Gynwyd" and insert --Bala Cynwyd--.

Item (57) ABSTRACT, Lines 2-3, delete "customer relationship (CRM)" and insert --customer relationship management (CRM)--.

In the Claims

Column 14, Line 30, Claim 12, delete "channel specific" and insert --channel-specific--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*